United States Patent [19]

Schaper et al.

[11] Patent Number: 4,624,802

[45] Date of Patent: Nov. 25, 1986

[54] SALICYLIC ACID ESTERS OF CARBOCYCLIC ALCOHOLS AS PERFUMES OR SCENTING AGENTS, PERFUMERY COMPOSITIONS AND SALICYLIC ACID ESTERS

[75] Inventors: Ulf-Armin Schaper; Benno Streschnak, both of Krefeld; Siegfried Bloesl, Duesseldorf; Walter Sommer, Krefeld, all of Fed. Rep. of Germany

[73] Assignee: Henkel Kommanditgesellschaft auf Aktien, Duesseldorf, Fed. Rep. of Germany

[21] Appl. No.: 688,129

[22] Filed: Jan. 2, 1985

[30] Foreign Application Priority Data

Jan. 7, 1984 [DE] Fed. Rep. of Germany ....... 3400342

[51] Int. Cl.[4] .......................... C11B 9/00; C07C 69/88

[52] U.S. Cl. .................................. 252/522 R; 560/67

[58] Field of Search ....................... 252/522 R, 522 A; 560/67

[56] References Cited

U.S. PATENT DOCUMENTS

| | | | |
|---|---|---|---|
| 3,714,227 | 1/1973 | Ueno et al. | 560/67 |
| 4,276,431 | 6/1981 | Schnegg et al. | 560/67 |

FOREIGN PATENT DOCUMENTS

| | | | |
|---|---|---|---|
| 144002 | 11/1902 | Fed. Rep. of Germany | 560/67 |
| 406225 | 9/1922 | Fed. Rep. of Germany | 560/67 |
| 7313202 | 3/1974 | Netherlands | 560/67 |

OTHER PUBLICATIONS

International Search Report.

Chemical Abstracts, Band 98, Nr. 16, Apr. 18, 1983, Columbus, Ohio (U.S.) siehe Seite 364, Zusammenfassung, 132150g, ES,A, 506622 (Traumhaft S.A.) Oct. 1, 1982.

S. Arctander: "Perfume and Flavor Chemicals" (Aroma Chemicals) I herausgegeben 1969, Montclair, N.J. (U.S.) siehe Nummern 218,340,529,530,783,1628,1680,1906,2241.

Chemical Abstracts, Band 76, Nr. 23, Jun. 5, 1972, Columbus, Ohio (U.S.) & SU,A, (Arbuzov A. E., Institute of Organic and Physical Chemistry) Jan. 26, 1972, siehe Seite 424, Zusammenfassung 140228z.

*Primary Examiner*—Werren B. Lone

*Attorney, Agent, or Firm*—Ernest G. Szoke; Nelson Littell, Jr.; Henry E. Millson, Jr.

[57] ABSTRACT

The process of scenting, comprising the steps of treating the material to be scented with an application of scenting-effective amount of a scenting agent, the improvement consisting of using a salicylic acid ester having the formula:

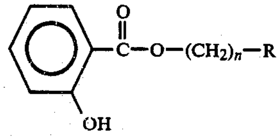

wherein R is a member having from 5 to 9 carbon atoms selected from the group consisting of cycloalkyl, $C_1$–$C_4$-alkylcycloalkyl, cycloalkenyl and $C_1$–$C_4$-alkylcycloalkenyl, and n is an integer from 0 to 3, as said scenting agent; more particularly using cyclohexyl salicylate or cyclopentyl salicylate as said scenting agent; as well as perfumery compositions containing said scenting agents; and salicylic acid ester scenting agents selected from the group consisting of:

(a) Cyclopentyl salicylate,
(b) 2,2,4-(2,4,4-)trimethylcyclopentyl salicylate in the form of an isomer mixture,
(c) 4-isopropylcyclohexyl salicylate,
(d) cyclohexylmethyl salicylate,
(e) cycloheptyl salicylate
(f) cyclooctyl salicylate, and
(g) cyclooct-4-enyl salicylate.

17 Claims, No Drawings

SALICYLIC ACID ESTERS OF CARBOCYCLIC ALCOHOLS AS PERFUMES OR SCENTING AGENTS, PERFUMERY COMPOSITIONS AND SALICYLIC ACID ESTERS

BACKGROUND OF THE INVENTION

Numerous esters of salicylic acid are known from the literature. Some of them, including for example methyl, butyl, amyl, hexyl, benzyl and 3-hexenyl salicylate, are used in the perfume industry (S. Arctander, Perfume and Flavor Chemicals, 1969; O. Z. Bedoukian, Perfum. Flavor 6 (5) 60–61 (1981)).

These esters of salicylic acid have attractive odor nuances and good persistency. However, scenting agents with a high persistency are still required.

OBJECTS OF THE INVENTION

An object of the present invention is the development of an improvement in the process of scenting, comprising the steps of treating the material to be scented with an application of a scenting-effective amount of a scenting agent, the improvement consisting of using a salicylic acid ester having the formula:

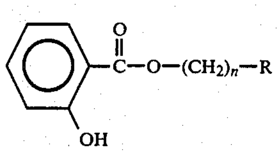

wherein R is a member having from 5 to 9 carbon atoms selected from the group consisting of cycloalkyl, $C_1$–$C_4$-alkylcycloalkyl, cycloalkenyl and $C_1$–$C_4$-alkylcycloalkenyl, and n is an integer from 0 to 3, as said scenting agent.

Another object of the present invention is the use of a salicylic acid ester having the formula:

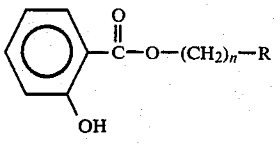

wherein R is a member having from 5 to 9 carbon atoms selected from the group consisting of cycloalkyl, $C_1$–$C_4$-alkylcycloalkyl, cycloalkenyl and $C_1$–$C_4$-alkylcycloalkenyl, and n is an integer of from 0 to 3, as a perfume.

A further object of the present invention is the development of perfumery compositions comprising from 1% to 50% by weight of at least one salicylic acid ester having the formula:

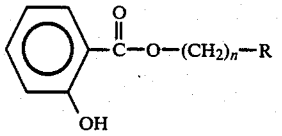

wherein R is a member having from 5 to 9 carbon atoms selected from the group consisting of cycloalkyl, $C_1$–$C_4$-alkylcycloalkyl, cycloalkenyl and $C_1$–$C_4$-alkylcycloalkenyl, and n is an integer from 0 to 3, and the remainder to 100% customary perfumery ingredients.

A yet further object of the present invention is the obtaining of salicylic acid ester scenting agents selected from the group consisting of:

(a) Cyclopentyl salicylate,
(b) 2,2,4-(2,4,4-)trimethylcyclopentyl salicylate in the form of an isomer mixture,
(c) 4-isopropylcyclohexyl salicylate,
(d) cyclohexylmethyl salicylate,
(e) cycloheptyl salicylate
(f) cyclooctyl salicylate, and
(g) cyclooct-4-enyl salicylate These and other objects of the present invention will become more apparent as the description thereof proceeds.

DESCRIPTION OF THE INVENTION

A new group of salicylic acid esters distinguished by surprising and valuable perfume properties, particularly by high persistence, has now been found. The group of salicylic acid esters in question are the salicylic acid esters of carbocyclic, non-aromatic alcohols. The esters are characterized by the following general formula:

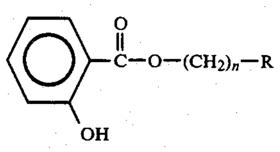

in which:

R represents cycloalkyl or cycloalkenyl optionally substituted by one or more by $C_1$–$C_4$-alkyls, the sum of the carbon atoms in R amounting to between 5 and 9, and n=0–3.

More particularly, the present invention relates to the improvement in the process of scenting, comprising the steps of treating the material to be scented with an application of a scenting-effective amount of a scenting agent, the improvement consisting of using a salicylic acid ester having the formula:

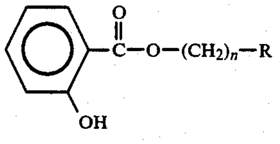

wherein R is a member having from 5 to 9 carbon atoms selected from the group consisting of cycloalkyl, $C_1$–$C_4$-alkylcycloalkyl, cycloalkenyl and $C_1$–$C_4$-alkylcycloalkenyl, and n is an integer from 0 to 3, as said scenting agent; perfumery compositions containing said acid esters; and novel salicylic acid ester scenting agents selected from the group consisting of:

(a) Cyclopentyl salicylate,
(b) 2,2,4-(2,4,4-)trimethylcyclopentyl salicylate in the form of an isomer mixture,
(c) 4-isopropylcyclohexyl salicylate,
(d) cyclohexylmethyl salicylate,
(e) cycloheptyl salicylate
(f) cyclooctyl salicylate, and
(g) cyclooct-4-enyl salicylate By virtue of their pronounced odor profile, the esters in which the sum of the carbon atoms in R amounts to between 5 and 6 and n=0 or 1 are particularly prominent.

The salicylic acid esters are produced in known manner by esterifying salicylic acid with a carbocyclic alcohol as defined in the general formula, optionally in the presence of acidic or alkaline catalysts, the water given off during the reaction being removed; or by reacting salicylic acid chloride with the alkali alcoholate of the carbocyclic alcohol; or by transesterifying methyl salicylate with the carbocyclic alcohol.

Some of the compounds corresponding to the general formula are known from the literature although there is no reference there to their properties as perfumes.

Others which have particularly interesting perfume properties are new compounds, and, accordingly, are claimed as such.

The odor characteristic of the salicylic acid esters in question is generally flowery with a typical salicylate note, flowery, aromatic, balsamy notes crucially determining the odor profile in individual cases.

The claimed esters may be combined with other perfumes and/or standard perfume ingredients to form new interesting perfume compositions. To this end, the compounds are used in a quantity of from 1 to 50% by weight, based on the composition as a whole. Compositions such as these may be used for perfuming cosmetics, such as toilet waters, creams, lotions, aerosols, toilet soaps, in extract perfumery and also for improving the odor of industrial products, such as cleaners, disinfectants, fabric treatment preparations and the like. By virtue of their unusual power of radiation and persistence, the esters are particularly suitable for perfuming textile washing agents or detergents, fabric softeners and cosmetics. The compositions or compounds in question are added to the various products in quantities of from 0.05% to 2% by weight, based on the product as a whole.

The salicylic acid esters of the invention are further distinguished by extremely high stability of their odor profile. They do not produce any unpleasant secondary odors, even after prolonged storage of the products perfumed or scented with them. The cyclopentyl and cyclohexyl esters are particularly preferred for use under practical conditions by virtue of their radiant odor and their persistence coupled with their high stability to aggressive media.

The following examples are illustrative of the practice of the invention without being limitative thereto in any manner.

EXAMPLES

General Procedure for the Esterification Process 1 mol of methyl salicylate and 2 moles of the particular alcohol are initially introduced into a reaction vessel. 18 gm (0.1 mol) of a 30% sodium methylate solution are slowly added dropwise with stirring at 60° to 65° C. On completion of the addition, the methanol released is distilled off through a distillation head, the sump temperature rising to approximately 170° C.

On completion of the transesterification reaction, the residue is taken up in water and extracted with ether. The ether extract is washed until neutral, dried over sodium sulfate and concentrated.

The crude product gives the desired ester after distillation through a packed column.

1. Cyclopentyl salicylate
(new compound)
B.p.$_{0.5}$ 114° C.
$n_D^{20}$ = 1.5355
Odor: very strong, sweet, flowery note 2. 2,2,4-(2,4,4-) trimethylcyclopentyl salicylate
(new compound,
isomer mixture)
B.p.$_{0.3}$ 108° C.
$n_D^{20}$ = 1.5145
Odor: faint balsamy note 3. 3,3,5-trimethylcyclohexyl salicylate
(CAS Registrg. No. (118-56-9))
$n_D^{20}$ = 1.5188
Odor: faint balsamy note 4. Cyclohexyl salicylate
(literature: R. De Fazius and
G. Berti, Ann. Chimica
41 621-641 (1951)).
B.p.$_{0.04}$ 115° C.
$n_D^{20}$ = 1.5335
Odor: aromatic note with a woody undertone 5. 4-isopropylcyclohexyl salicylate
(new compound)
M.p.
48° C.
Odor: faint balsamy note 6. Cyclohexylmethyl salicylate
(new compound)
B.p.$_{0.01}$ 100° C.
$n_D^{20}$ = 1.5309
Odor: faint balsamy note 7. Cycloheptyl salicylate
(new compound)
B.p.$_{0.01}$ 112° C.
$n_D^{20}$ = 1.5362
Odor: fine spicy-balsamy note 8. Cyclooctyl salicylate
(new compound)
$n_D^{20}$ = 1.5376
Odor: fine balsamy note 9. Cyclooct-4-enyl salicylate
(new compound)
B.p.$_{0.01}$ 130° C.
$n_D^{20}$ = 1.5467
Odor: faint, balsamy, slightly fatty note.

| 10. Flower complex | |
|---|---|
| Jasmacyclat(R) | 35 parts by weight |
| Jasmonan(R) | 25 parts by weight |
| Jasmelia(R) | 15 parts by weight |
| Aurantesin B(R) | 15 parts by weight |
| Eugenol pure | 85 parts by weight |
| Indolene | 180 parts by weight |
| Benzyl benzoate | 120 parts by weight |
| Benzyl acetate | 175 parts by weight |
| Cyclohexyl salicylate | 350 parts by weight |
| | 1,000 parts by weight |

11. PERFUMING OF SOAP

Cyclohexyl salicylate was incorporated in a concentration of 1.5% in soap chips. The forearm of a test subject was washed with the soap for 15 seconds and the odor of the lather assessed. The lather was then rinsed off, the forearm dried and the remaining odor assessed over a period of several hours.

The known scenting agent, benzyl salicylate, was used for comparison. A test panel of 15 people determined the power of performance and persistence and the average values are reported. Power of performance and persistance were assessed on a scale of 1 to 6, 6=very strong performance and persistence
5=strong performance und persistence
4=good performance and persistence
3=still noticeable performance and persistence
2=very faint performance and persistence 1=no performance or persistence The results are reported in Table I.

TABLE I

| | Odor of lather | Odor of skin |
|---|---|---|
| Cyclohexyl salicylate | 5 | 5 |
| Benzyl salicylate (comparison substance) | 3 | 3 |

12. PERFUMING A FABRIC SOFTENER 0.3% of cyclohexyl salicylate was incorporated as perfume or scenting agent in the formulation of a standard, commercially available fabric softener based on cation-active quaternary ammonium compounds, emulsifiers, viscosity regulators, solvents and diluents.

The same formulation perfumed with 0.3% of benzyl salicylate was used for comparison.

Three different cloths of cotton (CN), polyester (PE) and cotton/polyester blend (M) were rinsed with 100 ml of this fabric softener in the rinse cycle in a washing machine. After spin-drying, the cloths were assessed for odor both in moist form and after drying (overnight on a clothes-line) as in Example 11. In addition, the cloths were stored under dry conditions (in polyethylene bags) and reassessed after various periods. The results are reported in Table 2.

TABLE 2

| | Fabric | Moist Wash | Dried over-night | +24 h | +1 week | +2 weeks |
|---|---|---|---|---|---|---|
| Cyclohexyl salicylate | CN | 6 | 5 | 5 | 5 | 4 |
| | PE | 6 | 6 | 5 | 5 | 4 |
| | M | 5 | 5 | 5 | 4 | 3 |
| Benzyl salicylate (comparison substance) | CN | 4 | 3 | 2 | 3 | 1 |
| | PE | 4 | 3 | 2 | 2 | 1 |
| | M | 3 | 3 | 2 | 2 | 1 |

13. PERFUMING A DETERGENT COMPOSITION 0.15% of cyclohexyl salicylate was incorporated as scenting agent or perfume in the formulation of a standard commercially available heavy-duty detergent composition based on anionic and nonionic tensides, builders, complexing agents, perborate, redeposition inhibitors, soil suspending agents, brighteners and fillers. A second sample of the same detergent composition was perfumed with 0.15% of benzyl salicylate for comparison.

Normally soiled wash was washed with the detergents in a drum-type washing machine using the pre-wash and main wash cycles.

On completion of both the pre-wash and main wash cycles, (a) the wash liquor was assessed for odor, and (b) after rinsing and spin-drying, the damp wash was assessed for odor in the same way as described in Example 11. The results are given in Table 3.

TABLE 3

| | Odor of the wash liquor | | |
|---|---|---|---|
| | After Pre-wash Cycle | After Main-wash Cycle | Damp wash |
| Cyclohexyl salicylate | 5 | 5 | 3 |
| Benzyl salicylate (comparison substance) | 2 | 2 | 2 |

The preceding specific embodiments are illustrative of the practice of the invention. It is to be understood, however, that other expedients known to those skilled in the art or described herein may be employed without departing from the spirit of the invention or the scope of the appended claims.

We claim:

1. In the process of scenting, comprising the steps of treating the material to be scented with an application of a scenting-effective amount of a scenting agent, the improvement consisting of using a salicylic acid ester having the formula:

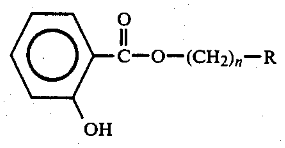

wherein R is a cyclic group having from 5 to 9 carbon atoms selected from the group consisting of cycloalkyl, $C_1$-$C_4$-alkylcycloalkyl, cycloalkenyl and $C_1$-$C_4$-alkylcycloalkenyl, and n is an integer from 0 to 3, as said scenting agent.

2. The process of claim 1 wherein the carbon atoms in R is 5 or 6 and n=0 or 1.

3. The process of claim 1 wherein said salicylic acid ester is cyclohexyl salicylate.

4. The process of claim 1 wherein said salicylic acid ester is cyclopentyl salicylate.

5. The use of a salicylic acid ester having the formula:

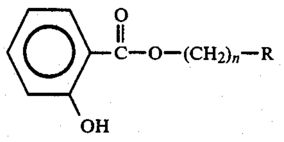

wherein R is a cyclic group having from 5 to 9 carbon atoms selected from the group consisting of cycloalkyl, $C_1$-$C_4$-alkylcycloalkyl, cycloalkenyl and $C_1$-$C_4$-alkylcycloalkenyl, and n is an integer of from 0 to 3, as a perfume.

6. Perfumery compositions comprising from 1% to 50% by weight of at least one salicylic acid ester having the formula:

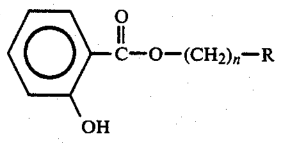

wherein R is a cyclic group having from 5 to 9 carbon atoms selected from the group consisting of cycloalkyl, $C_1$-$C_4$-alkylcycloalkyl, cycloalkenyl and $C_1$-$C_4$-alkylcycloalkenyl, and n is an integer from 0 to 3, and the remainder to 100% of customary perfumery ingredients.

7. The perfumery composition of claim 6 wherein the carbon atoms in R is 5 or 6 and n=0 or 1.

8. The perfumery composition of claim 6 wherein said salicylic acid ester is cyclohexyl salicylate.

9. The perfumery composition of claim 6 wherein said salicylic acid ester is cyclopentyl salicylate.

10. Salicylic acid ester compounds useful as scenting agents selected from the group consisting of:

(a) Cyclopentyl salicylate,
(b) 2,2,4-(2,4,4-)trimethylcyclopentyl salicylate in the form of an isomer mixture,
(c) 4-isopropylcyclohexyl salicylate,
(d) cyclohexylmethyl salicylate,
(e) cycloheptyl salicylate
(f) cyclooctyl salicylate, and
(g) cyclooct-4-enyl salicylate.

11. The salicylic acid ester of claim 10 being which is cyclopentyl salicylate.

12. The salicylic acid ester of claim 10 which is 2,2,4-(2,4,4-)trimethylcyclopentyl salicylate in the form of an isomer mixture.

13. The salicylic acid ester of claim 10 which is 4-isopropylcyclohexyl salicylate.

14. The salicylic acid ester of claim 10 which is cyclohexyl salicylate.

15. The salicylic acid ester of claim 10 which is cycloheptyl salicylate.

16. The salicylic acid ester of claim 10 which is cyclooctyl salicylate.

17. The salicylic acid ester of claim 10 which is cyclooct-4-enyl salicylate.

* * * * *